US009738612B2

(12) United States Patent
Li et al.

(10) Patent No.: US 9,738,612 B2
(45) Date of Patent: Aug. 22, 2017

(54) METHYLACRYLOYL BENZIMIDAZOLONE DERIVATIVE AND ANTI-TUMOUR USE THEREOF

(71) Applicant: SHANGHAI NATURE STANDARD R&D AND BIOTECH CO., LTD, Shanghai (CN)

(72) Inventors: Jiapeng Li, Shanghai (CN); Zhiqin Ji, Shanghai (CN); Xiaoya Zhou, Shanghai (CN); Shaopeng Wei, Shanghai (CN); Yong Qian, Shanghai (CN); Tianpei Xie, Shanghai (CN)

(73) Assignees: Shanghai Nature Standard R&D and Biotech Co., Ltd, Shanghai (CN); Shanghai Standard Technology Co., Ltd., Shanghai (CN); Shanghai Founder Biomed R&D Co., Ltd., Shanghai (CN)

( * ) Notice: Subject to any disclaimer, the term of this patent is extended or adjusted under 35 U.S.C. 154(b) by 0 days.

(21) Appl. No.: 15/128,655

(22) PCT Filed: Mar. 23, 2015

(86) PCT No.: PCT/CN2015/074896
§ 371 (c)(1),
(2) Date: Jan. 25, 2017

(87) PCT Pub. No.: WO2015/144029
PCT Pub. Date: Oct. 1, 2015

(65) Prior Publication Data
US 2017/0144976 A1    May 25, 2017

(30) Foreign Application Priority Data

Mar. 23, 2014 (CN) .......................... 2014 1 0109156

(51) Int. Cl.
C07D 401/14       (2006.01)
A61K 31/437      (2006.01)
C07D 235/26      (2006.01)
C07D 471/04      (2006.01)

(52) U.S. Cl.
CPC ......... *C07D 235/26* (2013.01); *C07D 471/04* (2013.01)

(58) Field of Classification Search
CPC ........................... C07D 401/14; A61K 31/437
USPC ............................................ 546/119; 514/303
See application file for complete search history.

(56) References Cited

U.S. PATENT DOCUMENTS 8,138,347 B2 * 3/2012 Knight ................. C07D 285/24
544/105

FOREIGN PATENT DOCUMENTS

CN          102503896        6/2012

OTHER PUBLICATIONS

International Search Report for PCT/CN2015/074896, dated Jun. 29, 2015, 5 pages including English translation.

* cited by examiner

*Primary Examiner* — Niloofar Rahmani
(74) *Attorney, Agent, or Firm* — Hamre, Schumann, Mueller & Larson, P.C.

(57) ABSTRACT

Disclosed are a use of a methylacryloyl benzimidazolone derivative, an optical isomer or a pharmaceutically acceptable salt or prodrug thereof in the preparation of: (a) a pharmaceutical composition or reagent for down-regulating the activity of PI3K/Akt pathways; (b) a pharmaceutical composition or reagent for treating or inhibiting a tumour; and/or inhibiting tumour cell growth; and/or (c) a pharmaceutical composition or reagent for blocking the cell cycle. The compounds involved in the present invention can down-regulate the level of Akt phosphorylation in P13K/Akt signaling pathways, and the functional effects of the compounds are equivalent to those of a novel small-molecular targeting drug MK2206; while the research at the cellular level has found that the methylacryloyl benzimidazolone derivatives represented by FD1 have a good proliferation inhibiting effect on tumour cells. What is different from MK2206 is that FD1 has better effects on a PTEN deleted cell.

7 Claims, 3 Drawing Sheets

METHYLACRYLOYL BENZIMIDAZOLONE DERIVATIVE AND ANTI-TUMOUR USE THEREOF

TECHNICAL FIELD

The present invention belongs to biomedical field, and particularly relates to the use of methylacryloyl benzimidazolone derivative for antitumor.

BACKGROUND ART

Currently tumour is the most serious public health problem mankind is facing, and recently itcauses millions of deaths worldwide each year. Developing anti-tumor drugs with high efficacies and low toxicitities is the key to tumor therapy. At present, the focus of the research and development of anti-tumour drugs has shifted from cytotoxic drugs to targeted therapy drug. The success in marketing imatinibmakes people see the hope for curing tumor, thereby small molecular targeted drug development has entered a vigorous period and various inhibitors of tumour-associated signaling pathways enter the market and achieved great success.

Previous studies have found that aberrant activation of PI3K/Akt signaling pathway, in which Akt phosphorylation and then activation is a key step, is present in a variety of tumors. Simultaneous activation of the T308 and S473 sites of Akt is necessary for Akt activation. The development of PI3K/Akt signaling pathway inhibitors has become a hot spot in the research and development of antitumour drugs. There are dozens of this typeof drugs in clinical trials so far, and MK2206 and Triciribine are two typicaldrugs of such kind with significant clinical efficacies, and have a very good prospect for further development. Since the PI3K/Akt signaling pathway aberrant activation exists prevalently in tumors, the successful development of such drugs will achieve good social and economic benefits.

Benzimidazolone is an oxidized derivative of the carbon atom at the 2-position of imidazole ring, and has been widely used as an intermediate in dye industry (Jolanta S.et al. Dyes and pigments. 2001, 15-27). In addition, the benzimidazole derivatives also are widely used clinically because they possess significant pharmacological activity. For example, oxatomide, a second-generation anti-histamine drug, belongs to benzimidazole derivatives (Iwamoto K., et al. Arzneimittel-forschung-drug Research. 2001, 51: 971-976). In a Chinese patent application CN201110326737.9, the applicants introduce methylacryloyl group on nirogen at 3-position of benzimidazolone, resulting methylacryloyl-benzimidazolone (methylacryloyl-benzimidazole (thio) ketone) derivatives that show a extremely high antibacterial activity. Also in this patent application a method for preparing such compounds has been disclosed, and concrete chemical structures are presented.

SUMMARY OF INVENTION

One object of the present invention is to provide a use of methylacryloyl benzimidazolone derivative for anti-tumor therapy.

In the first aspect of the present invention, it provides a use of methylacryloyl benzimidazolone derivative, an optical isomer thereof, or a pharmaceutically acceptable salt or prodrug thereof for preparing:

(a) a pharmaceutical composition or agent for down-regulating the activity of PI3K/Akt pathway;

(b) a pharmaceutical composition or agent for treating or inhibiting tumor and/or tumor cell growth;

(c) a pharmaceutical composition or agent for arresting cell cycle; and/or (d) a pharmaceutical composition or agent for inhibiting the activity of mTOR kinase.

In another preferred embodiment, the methylacryloyl benzimidazolone derivative has the structure of Formula I;

I

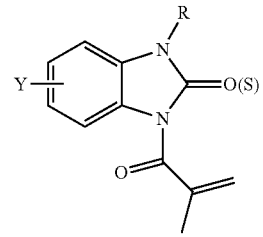

wherein:

R represents:

hydrogen; $C_1\sim C_8$ alkyl; or $C_1\sim C_8$ alkyl optionally substituted by cyano, halogen, benzene ring, $C_1\sim C_4$ alkoxy or $C_1\sim C_4$ alkylthio; $C_3\sim C_8$ alkenyl or $C_3\sim C_8$ alkynyl; or $C_3\sim C_8$ alkenyl or $C_3\sim C_8$ alkynyl optionally substituted by cyano, halogen, $C_1\sim C_4$ alkoxy or $C_1\sim C_4$ alkylthio; phenyl or phenyl optionally substituted by 1~3 substituents selected from the group consisting of halogen, $C_1\sim C_8$ alkyl, $C_3\sim C_8$ cycloalkyl, hydroxyl, $C_1\sim C_4$ alkoxy, $C_1\sim C_4$ haloalkyl, $C_1\sim C_4$ haloalkoxy, $C_1\sim C_4$ haloalkylthio, $C_1\sim C_4$ haloalkyl sulfonyl, carboxy, nitro, cyano, phenyl, phenoxy, benzoyl;

Y represents:

Hydrogen; or 1~4 substituents selected from the group consisting of halogen, nitro, $C_1\sim C_8$ alkyl, $C_3\sim C_8$ cycloalkyl, $C_1\sim C_4$ haloalkyl;

wherein, when Y represents hydrogen, R is not isoprepenyl;

or Y represents:

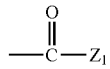

wherein, $Z_1$ represents hydroxyl, $C_1\sim C_8$ alkoxy, $C_3\sim C_8$ alkenyloxy or $C_3\sim C_8$ alkynyloxy, amino, or amino substituted with one or two $C_1\sim C_8$ alkyl;

or Y represents:

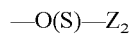

wherein, $Z_2$ represents hydrogen, $C_1\sim C_4$ alkyl, $C_3\sim C_8$ alkenyl or $C_3\sim C_8$ alkynyl, $C_1\sim C_4$ haloalkyl, $C_1\sim C_8$ aliphatic acyl, $C_1\sim C_8$ haloaliphatic acyl, carbamoyl, N-methylcarbamoyl, N-ethylcarbamoyl, N, N-dimethylcarbamoyl, N, N-diethylcarbamoyl, phenyl, benzoyl, phenylacetyl, phenylsulfonyl or phenyl, benzoyl, phenylsulfonyl optionally substituted with 1~3 substituents selected from the group consisting of: halogen, $C_1\sim C_8$ alkyl, $C_3\sim C_8$ cycloalkyl, hydroxyl, $C_1\sim C_4$ alkoxy, $C_1\sim C_4$ haloalkyl, $C_1\sim C_4$ haloalkoxy, $C_1\sim C_4$ haloalkylthio, $C_1\sim C_4$ haloalkylsulfonyl, carboxy, nitro, and cyano;

or Y represents:

wherein, $Z_3$ represents hydrogen, $C_1{\sim}C_8$ alkyl, $C_3{\sim}C_8$ cycloalkyl, $C_3{\sim}C_8$ alkenyl, $C_3{\sim}C_8$ alkynyl, $C_1{\sim}C_4$ haloalkyl, $C_1{\sim}C_8$ acyl, or a 5- or 6-membered heterocyclic group having 1~3 heteroatoms selected from nitrogen, oxygen and sulfur, phenyl, benzoyl, phenylacetyl, phenylsulfonyl, or phenyl, benzoyl, phenylsulfonyl optionally substituted with 1~3 substituents selected from the group consisting of: halogen, $C_1{\sim}C_8$ alkyl, $C_3{\sim}C_8$ cycloalkyl, hydroxy, $C_1{\sim}C_4$ alkoxy, $C_1{\sim}C_4$ haloalkyl, $C_1{\sim}C_4$haloalkoxy, $C_1{\sim}C_4$ haloalkylthio, haloalkylsulfonyl, carboxy, nitro, cyano; $Z_4$ represents hydrogen, $C_1{\sim}C_8$ alkyl, $C_3{\sim}C_8$ cycloalkyl, $C_3{\sim}C_8$ alkenyl, $C_3{\sim}C_8$ alkynyl, $C_1{\sim}C_4$ haloalkyl, or $Z_3$ and $Z_4$ together with the nitrogen atom to which they are attached form a 5-7-membered heterocyclic group which may contain one or two or more than two heteroatoms selected from nitrogen and oxygen in addition to the nitrogen atom.

In another preferred embodiment, R represents: hydrogen, ethyl, n-propyl, isopropyl, propenyl, isopropenyl, 2-cyanoethyl, benzyl, 2-fluoroethyl, 2-chloroethyl, 2-bromoethyl, 2-methoxyethyl, 2-methoxypropyl, 2-methoxyisopropyl, 2-ethoxyethyl, 2-ethoxypropyl, 2-ethoxyisopropyl, phenyl or phenyl optionally substituted with 1~3 substituents selected from the group consisting of: fluorine, chlorine, bromine, methyl, ethyl, n-propyl, isopropyl, cyclopropyl, hydroxy, methoxy, ethoxy, propoxy, isopropoxy, 2-chloroethyl, 2-chloropropyl, 2-chloroethoxy, 2-chloropropoxy, carboxy, nitro, cyano;

Y represents: hydrogen or 1-4 substituents selected from the group consisting of fluorine, chlorine, bromine, nitro, methyl, ethyl, n-propyl, isopropyl, 2-chloroethyl, 2-chloropropyl, 2-chlorobutyl, 2-bromoethyl, 2-bromopropyl, 2-bromobutyl;

wherein, when Y represents hydrogen, R is not isopropenyl;

or Y represents:

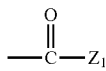

wherein, $Z_1$ represents hydroxyl, methoxy, ethoxy, n-propoxy, isopropoxy, n-butoxy, amino, N-methylamino, N-ethylamino, N, N-dimethylamino, N, N-diethylamino;

or Y represents:
—O(S)—$Z_2$ wherein, $Z_2$ represents hydrogen, methyl, ethyl, propyl, isopropyl, 2-chloromethyl, 2-chloroethyl, 2-chloropropyl, formyl, acetyl, phenyl, benzoyl, phenylsulfonyl, or phenyl, benzoyl, phenylacetyl, or phenylsulfonyl optionally substituted with 1~3 substituents selected from the group consisting of fluorine, chlorine, bromine, methyl, ethyl, propyl, isopropyl, 2-chloroethyl, 2-chloropropyl, cyclopropyl, hydroxy, methoxy, ethoxy, 2-chloroethyl, 2-chloropropyl, 2-chlorobutyl, 2-bromoethyl, 2-bromopropyl, 2-bromobutyl, chloromethoxy, 2-chloroethoxy, 2-chloropropoxy, bromomethoxy, 2-bromoethoxy, 2-bromopropoxy, carboxy, nitro, cyano;

or, Y represents:

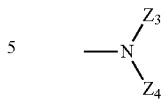

wherein, $Z_3$ represents hydrogen, methyl, ethyl, n-propyl, isopropyl, cyclopropyl, propenyl, isopropenyl, propynyl, 2-chloroethyl, 2-chloropropyl, 2-chlorobutyl, 2-bromoethyl, 2-bromopropyl, 2-bromobutyl, formyl, acetyl, n-propionyl, isopropionyl, phenyl, benzoyl, phenylacetyl, phenylsulfonyl, or phenyl, benzoyl, phenylsulfonyl optionally substituted with 1~3 substituents selected from the group consisting of halogen, $C_1{\sim}C_8$ alkyl, $C_3{\sim}C_8$ cycloalkyl, hydroxy, $C_1{\sim}C_4$ alkoxy, $C_1{\sim}C_4$ haloalkyl, $C_1{\sim}C_4$ haloalkoxy, $C_1{\sim}C_4$ haloalkylthio, $C_1{\sim}C_4$ haloalkylsulfonyl, carboxy, nitro, cyano; $Z_4$ represents hydrogen, methyl, ethyl, n-propyl, isopropyl, propenyl, isopropenyl, propynyl, 2-chloroethyl, 2-chloropropyl, 2-chlorobutyl, 2-bromoethyl, 2-bromopropyl, 2-bromobutyl, or $Z_3$ and $Z_4$ together with the nitrogen atom to which they are attached form a 5-7-membered heterocyclic group.

In another preferred embodiment, R represents : hydrogen, propenyl, isopropenyl, benzyl, 2-fluoroethyl, 2-chloroethyl, 2-bromoethyl, 2-methoxyethyl, 2-methoxypropyl, 2-methoxyisopropyl, 2-ethoxyethyl, 2-ethoxypropyl, 2-ethoxyisopropyl;

Y represents:

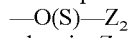

wherein, $Z_1$ represents hydroxyl, methoxy, ethoxy, n-propoxy, isopropoxy, n-butoxy, amino, N-methylamino, N-ethylamino, N, N-dimethylamino, N, N-diethylamino;

or Y represents:
—O(S)—$Z_2$ wherein, $Z_2$ represents hydrogen, formyl, acetyl, benzoyl, phenylsulfonyl, or benzoyl, phenylacetyl, or phenylsulfonyl optionally substituted with 1~3 substituents selected from the group consisting of fluorine, chlorine, bromine, hydroxy, methoxy, ethoxy, nitro, cyano;

or Y represents:

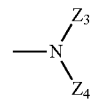

wherein, $Z_3$ represents hydrogen, formyl, acetyl, n-propionyl, isopropionyl, benzoyl, phenylacetyl, phenylsulfonyl; $Z_4$ represents hydrogen, methyl, ethyl, n-propyl, isopropyl, propenyl, isopropenyl, propynyl, 2-chloroethyl, 2-chloropropyl, 2-chlorobutyl, 2-bromoethyl, 2-bromopropyl, 2-bromobutyl, or $Z_3$ and $Z_4$ together with the nitrogen atom to which they are attached form a 5-7-membered heterocyclic group.

In another preferred embodiment, R represents : hydrogen, propenyl, isopropenyl, 2-fluoroethyl, 2-chloroethyl, 2-bromoethyl, 2-methoxyethyl, 2-methoxypropyl, 2-methoxyisopropyl;

Y represents:

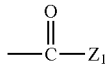

wherein, $Z_1$ represents hydroxyl, methoxy, ethoxy, n-propoxy, isopropoxy, n-butoxy.

In another preferred embodiment, the methylacryloyl benzimidazolone derivative has the structure of Formula II,

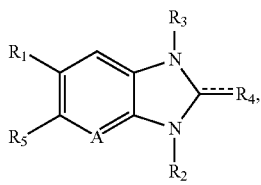
(II)

in Formula II,

A is C, or N;

$R_1$ and $R_5$ are each independently selected from hydrogen, halogen, C1~C10 alkyl, C2~C8 alkenyl, C2~C8 alkynyl, CN, $NO_2$;

$R_2$ and $R_3$ are each independently selected from hydrogen, halogen, C1~C10 alkyl, C2~C8 alkenyl, C2~C8 alkynyl, C3~C10 cycloalkyl, heterocyclic group, aryl, heteroaryl, C1~C10 aldehyde group, C2~C10 acyl, C2~C10 ester group, CN, $NO_2$;

$R_4$ is selected from O, S, halogen;

"=====" represents a single bond or a double bond;

the alkyl, alkenyl, alkynyl, cycloalkyl, heterocyclyl, aryl, heteroaryl, aldehyde group, acyl, ester group are substituted or unsubstituted, and/or linear or branched.

In another preferred embodiment, A is N.

In another preferred embodiment, $R_1$ is selected from hydrogen, halogen and trifluoromethyl.

In another preferred embodiment, $R_5$ is selected from hydrogen, halogen and trifluoromethyl.

In another preferred embodiment, $R_2$ and $R_3$ are each independently selected from substituted or unsubstituted C1~C8 alkyl, C2~C8 alkenyl, C2~C8 alkynyl, C2~C8 aldehyde group, C2~C8 acyl, C2~C8 ester group.

In another preferred embodiment, $R_4$ is O.

In another preferred embodiment, the pharmaceutical composition or agent is used to reduce the activation level of Akt.

In another preferred embodiment, the pharmaceutical composition or agent is further used to inhibit the phosphorylation of Akt.

In another preferred embodiment, the phosphorylation comprises the phosphorylation of the Akt S473 site.

In another preferred embodiment, the methylacryloyl benzimidazolone derivative is selected from the group consisting of compounds represented by the formulas FD1 to FD18 or a combination thereof:

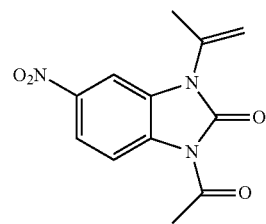
FD1

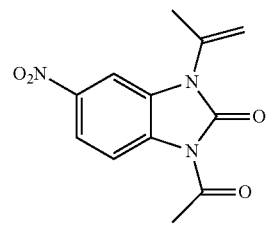
FD2

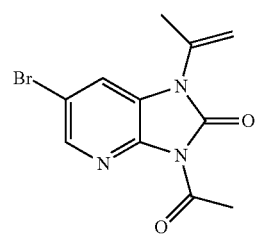
FD162

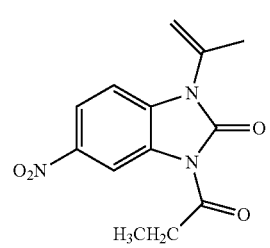
FD4

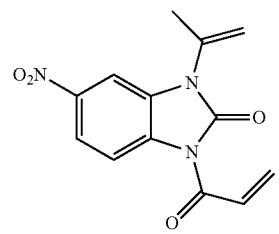
FD5

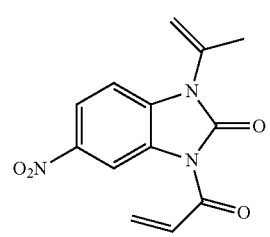
FD6

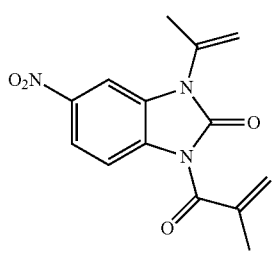
FD7
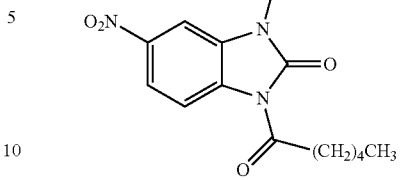
FD13
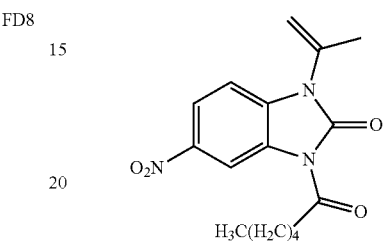
FD8
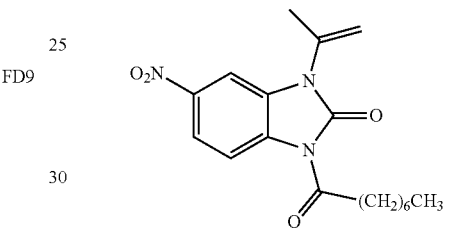
FD14
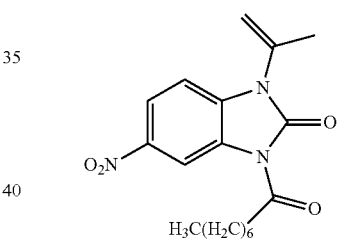
FD9
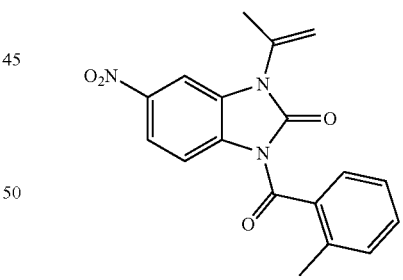
FD15
FD10
FD16
FD11
FD17
FD12
FD18

In another preferred embodiment, the methylacryloyl benzimidazolone derivative is selected from the compounds represented by the formulas FD1 and FD162 or a combination thereof:

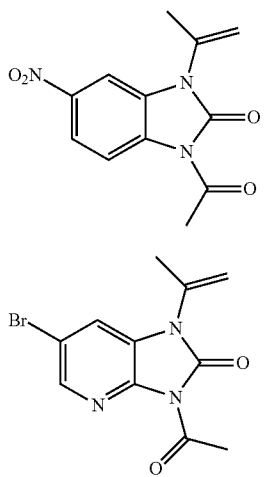

FD1

FD162

In another preferred embodiment, the tumor or tumor cell is a tumor or a cell of tumor selected from the group consisting of liver cancer, cervical cancer, glioma, colon cancer, kidney cancer, breast cancer, lung cancer, prostate cancer, pancreatic cancer, skin cancer, nasopharynx cancer, esophageal cancer, gastric cancer, ovarian cancer, and melanoma.

In another preferred embodiment, the tumor or tumor cell is a tumor or tumor cell with a PTEN mutation (decreased expression of PTEN) or deletion.

In another preferred embodiment, the tumor or tumor cell is prostate cancer or prostate cancer cell.

In another preferred embodiment, the tumor cell is selected from the group consisting of PC-3, A549, SGC-7901, Hela, H4, FHCC98, SMMC7721, BEL7404, A498, SW1116, MDA-MB-231, MDA-MB-468, DU145, U87-MG, Wi38, H1299, or a combination thereof.

In another preferred embodiment, the tumor cell is selected from the group consisting of PC-3, A549, SGC-7901, Hela, H4, FHCC98, SMMC7721, or a combination thereof.

In the second aspect of the present invention, it provides a pharmaceutical composition comprising: (a) a methylacryloyl benzimidazolone derivative, an optical isomer thereof, or a pharmaceutically acceptable salt or prodrug thereof; and (b) a pharmaceutically acceptable carrier.

In another preferred embodiment, the methylacryloyl benzimidazolone derivative comprises a compound of formula I.

In another preferred embodiment, the medicament or pharmaceutical composition further comprises a cytotoxic drug (e.g., but not limited to, a DNA interfering agent (e.g., cisplatin or doxorubicin)) and/or an antimetabolite drug (e.g., but are not limited to, pyrimidine antagonists, purine antagonists, folate antagonists).

In another preferred embodiment, the cytotoxic drug is selected from the group consisting of anthracycline antibiotics, paclitaxel, vinca alkaloids, camptothecin, alkylating agents, platinum or combinations thereof.

In another preferred embodiment, the antimetabolite drug is selected from the group consisting of methotrexate, 5-Fluorouracil, hydroxyurea, cytosine arabinoside, or a combination thereof.

In another preferred embodiment, in the medicament or pharmaceutical composition, the content of the methylacryloyl benzimidazolone derivative is 0.01 to 99 wt %, preferably 0.1 to 90 wt %.

In another preferred embodiment, the medicament or pharmaceutical composition is further used to induce tumor cell apoptosis.

In another preferred embodiment, the medicament or pharmaceutical composition is further used to interfere with tumor cell proliferation.

In another preferred embodiment, the medicament or pharmaceutical composition is further used to regulate the cell cycle of a tumor cell; and/or the medicament or pharmaceutical composition is further used to arrest cell cycle.

In another preferred embodiment, the medicament or pharmaceutical composition is used to induce G1 cell arresting in tumor cells.

In another preferred embodiment, the medicament or pharmaceutical composition is further used to inhibit metastasis of tumor cells.

In the third aspect of the present invention, it provides a non-therapeutic method in vitro for down-regulating the activity of PI3K/Akt pathway and/or regulating cell cycle, comprising a step of culturing the cell in the presence of a methylacryloyl benzimidazolone derivative, an optical isomer thereof, or a pharmaceutically acceptable salt or prodrug thereof thereby down-regulating the activity of PI3K/Akt pathway in the cell and/or regulating the cell cycle.

In another preferred embodiment, the cell is a tumor cell, preferably the tumor cell is a cell of tumor selected from the group consisting of liver cancer, cervical cancer, glioma, colon cancer, kidney cancer, breast cancer, lung cancer, prostate cancer, pancreatic cancer, skin cancer, nasopharynx cancer, esophageal cancer, gastric cancer, ovarian cancer, and melanoma.

In another preferred embodiment, the tumor cell is selected from the group consisting of PC-3, A549, SGC-7901, Hela, H4, FHCC98, SMMC7721, BEL7404, A498, SW1116, MDA-MB-231, MDA-MB-468, DU145, U87-MG, Wi38, H1299, or a combination thereof; more preferably selected from the group consisting of PC-3, A549, SGC-7901, Hela, H4, FHCC98, SMMC7721, or a combination thereof.

In another preferred embodiment, the effective concentration of the compound of Formula I is 0.01 nM-1 mM, preferably 0.1 nM-500 μM, and most preferably 1 nM-100 μM (micromoles per liter).

In another preferred embodiment, the action time of the compound of Formula I is 2~96h.

In another preferred embodiment, the action time of the compound of Formula I is 1~30 days.

In the forth aspect of the present invention, it provides an non-therapeutic method in vitro for inhibiting cell growth or inducing apoptosis comprising a step of culturing the cell in the presence of a methylacryloyl benzimidazolone derivative, an optical isomer thereof, or a pharmaceutically acceptable salt or prodrug thereof.

In another preferred embodiment, the cell is a tumor cell.

In another preferred embodiment, the effective concentration of the methylacryloyl benzimidazolone derivative is 0.01 nM/L-1 mM/L, preferably 0.1 nM/L-500 μM/L, and most preferably 0.1 nM/L-100 μM/L.

In another preferred embodiment, when the compound of Formula I acts in vitro, the action time of the compound of Formula I is 2~96h.

In the fifth aspect of the present invention, it provides a use of a methylacryloyl benzimidazolone derivative of Formula I or Formula II or a pharmaceutically acceptable salt thereof for preparing a composition, wherein the composition is used for one or more applications selected from the group consisting of:

(i) inhibiting tumor cell growth;
(ii) inducing tumor cell apoptosis;
(iii) interfering with tumor cell proliferation;
(iv) regulating cell cycle of tumor cell;
(v) inhibiting tumor cell metastasis;
(vi) down-regulating the activity of PI3K/Akt pathway;
(vii) reducing Akt activation level;
(viii) inhibiting the Akt phosphorylation;
(ix) inhibiting the Akt phosphorylation at S473 site;
(x) treating or preventing tumor;
(xi) reducing mTOR activation level;
(xii) inhibiting mTOR phosphorylation;
(xii) down-regulating the activity of PI3K/Akt/mTOR signaling pathway.

In another preferred embodiment, the composition is a pharmaceutical composition.

In the sixth aspect of the present invention, it provides a method for treating tumor comprising a step of administering a therapeutically effective amount of a compound of Formula I and/or Formula II, an optical isomer thereof, or a pharmaceutically acceptable salt or prodrug thereof, or a pharmaceutical composition thereof to a subject in need.

In another preferred embodiment, the administration lasts 1 to 360 days, preferably 1 to 180 days, more preferably 1 to 60 days.

In the seventh aspect of the present invention, it provides a pharmaceutical composition for treating or inhibiting tumor comprising (a) a pharmaceutically acceptable carrier and (b) a compound of Formula I and/or Formula II, an optical isomer thereof, or a pharmaceutically acceptable salt or prodrug thereof,

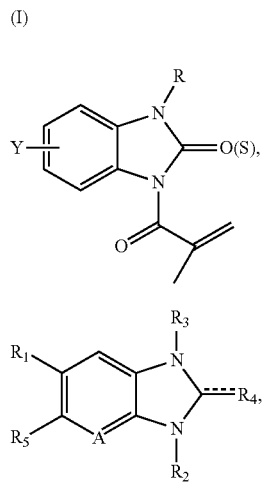

wherein, each group is as defined above.

In another preferred embodiment, the dosage form of the pharmaceutical composition is an oral dosage form, an injection.

In the eighth aspect of the present invention, it provides a kit, comprising:

a container, and a methylacryloyl benzimidazolone derivative of Formula I and/or Formula II, an optical isomer thereof, or a pharmaceutically acceptable salt or prodrug thereof contained therein, and a pharmaceutically acceptable carrier;

a specification describing that the methylacryloyl benzimidazolone derivative is used for one or more applications selected from the group consisting of:

(i) inhibiting tumor cell growth;
(ii) inducing tumor cell apoptosis;
(iii) interfering with tumor cell proliferation;
(iv) regulating cell cycle of tumor cell;
(v) inhibiting tumor cell metastasis;
(vi) down-regulating the activity of PI3K/Akt pathway;
(vii) reducing the Akt activation level;
(viii) inhibiting the Akt phosphorylation;
(ix) inhibiting the Akt phosphorylation at S473 site;
(x) treating or preventing tumor;
(xi) reducing mTOR activation level;
(xii) inhibiting mTOR phosphorylation;
(xii) down-regulating the activity of PI3K/Akt/mTOR signaling pathway.

In another preferred embodiment, the kit further comprises an additional anti-cancer medicament.

In the ninth aspect of the present invention, it provides a compound having the structure of Formula II,

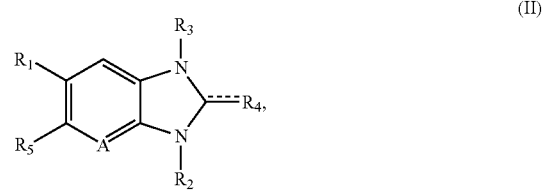

in Formula II,

A is selected from: C, and N;

$R_1$ and $R_5$ are each independently selected from hydrogen, halogen, C1~C10 alkyl, C2~C8 alkenyl, C2~C8 alkynyl, CN, $NO_2$;

$R_2$ and $R_3$ are each independently selected from hydrogen, halogen, C1~C10 alkyl, C2~C8 alkenyl, C2~C8 alkynyl, C3~C10 cycloalkyl, heterocyclic, aryl, heteroaryl, C1~C10 aldehyde group, C2~C10 acyl, C2~C10 ester group, CN, $NO_2$;

$R_4$ is selected from O, S, halogen;

"======" represents a single bond or a double bond;

the alkyl, alkenyl, alkynyl, cycloalkyl, heterocyclic, aryl, heteroaryl, aldehyde group, acyl, and ester group are substituted or unsubstituted, and/or linear or branched.

In another preferred embodiment, A is N.

In another preferred embodiment, $R_1$ is selected from hydrogen, halogen and trifluoromethyl.

In another preferred embodiment, $R_5$ is selected from hydrogen, halogen and trifluoromethyl.

In another preferred embodiment, $R_2$ and $R_3$ are each independently selected from substituted or unsubstituted C1~C8 alkyl, C2~C8 alkenyl, C2~C8 alkynyl, C2~C8 aldehyde group, C2~C8 acyl, C2~C8 ester group.

In another preferred embodiment, $R_4$ is O.
In another preferred embodiment, the compound is

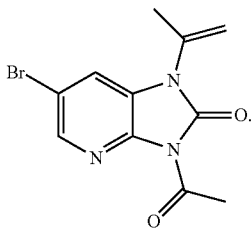 [SMILES: C=C(C)n1c(=O)n(C(C)=O)c2ncc(Br)cc21]

It should be understood that in the present invention, the technical features specifically described above and hereinafter (such as the Examples) can be combined with each other, thereby constituting a new or preferred technical solution, which needs not be specified one by one.

As shown in the figure, MK2206 (a candidate drug developed by Merck, in Phase II clinical trial), FD1 and FD162 can significantly reduce the Akt phosphorylation level. Inhibition of Akt hyperactivity that commonly existed in tumors is an important strategy for the development of oncology drugs. The results indicate that the FD series of compounds act similarly to MK2206, and both of them can significantly inhibit the Akt phosphorylation and thus play an antitumor effect.

Figure 2:
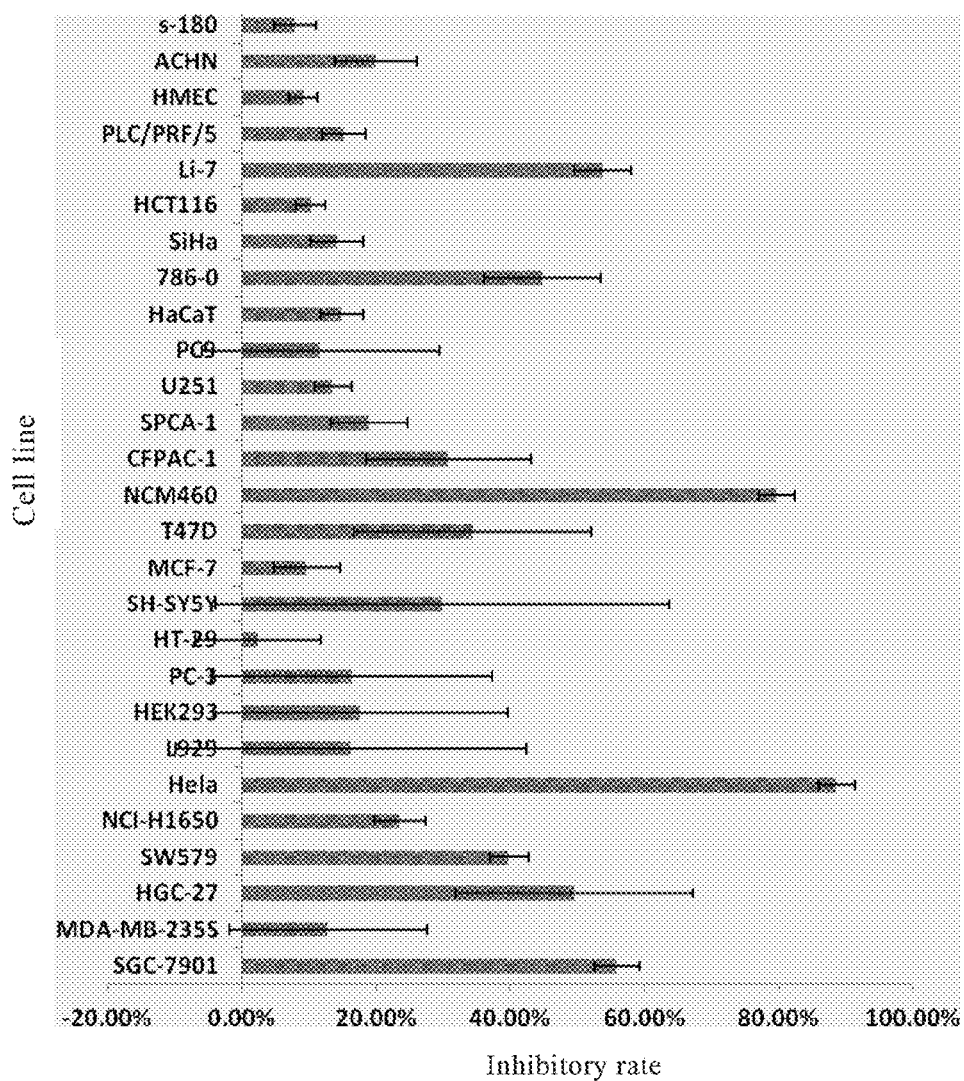

FIG. 2 shows that the compounds of the present invention are able to generally inhibit the proliferation of tumor cells, and have extremely high inhibition to Hela cell proliferation.

Figure 3:
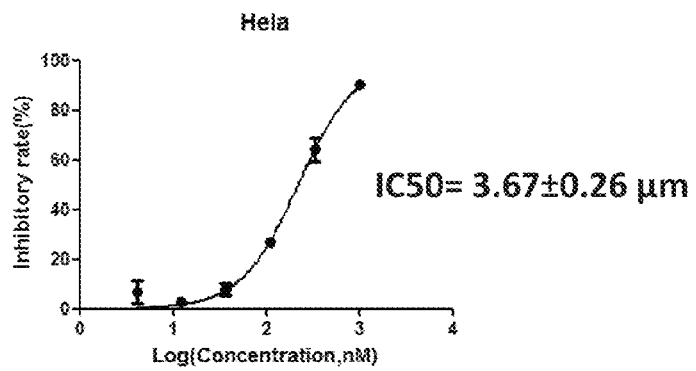

FIG. 3 shows that the half inhibitory concentration of the compound of the invention against Hela cell proliferation was 3.67 micromole.

Figure 4:
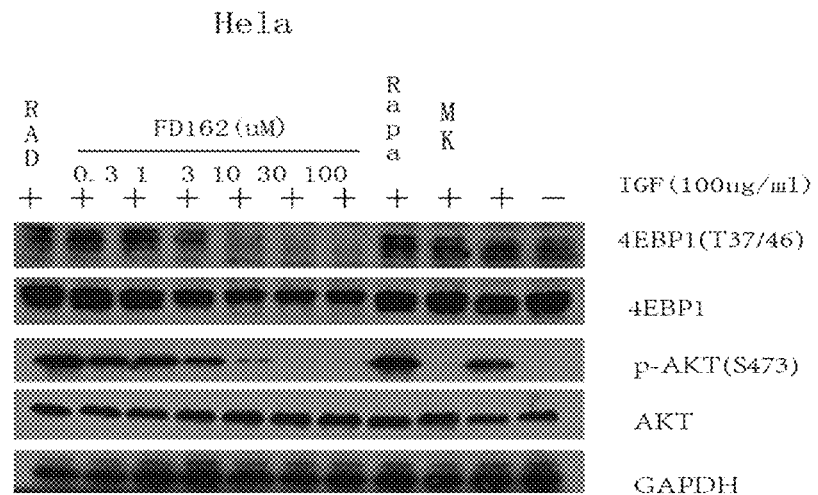

FIG. 4 shows that the compounds of the present invention are capable of down-regulating PI3K/Akt/mTOR signaling pathway in a concentration-dependent manner.

Figure 5:
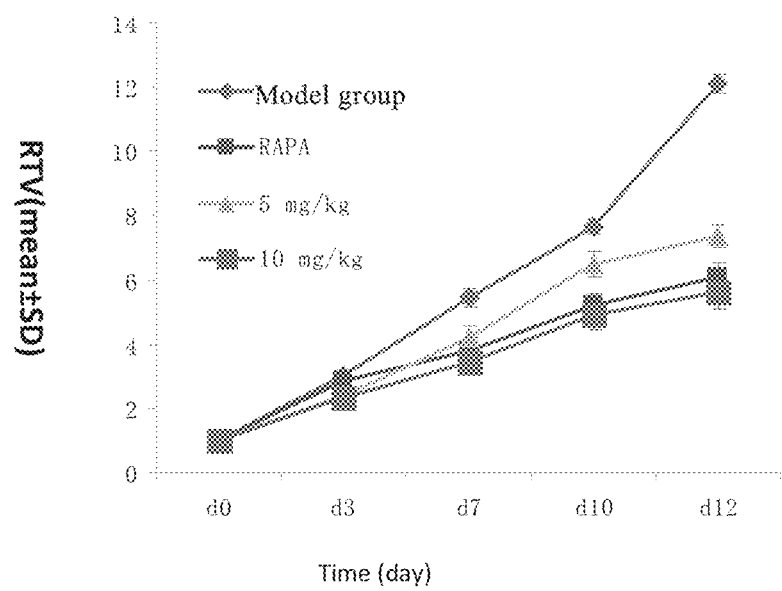

FIG. 5 shows the tumor inhibiting effect of the compounds of the present invention.

DETAILED DESCRIPTION OF INVENTION

After an intensive and long-term research, the inventors have unexpectedly discovered that methylacryloyl benzimidazolone derivatives could effectively inhibit the growth of tumor cells. Further experiments demonstrate that these compounds could effectively inhibit PI3K/Akt signaling pathway. Based on the above, the inventors have completed the present invention.

Specifically, the experimental results show that methylacryloyl benzimidazolone derivatives (FD series) can significantly inhibit the Akt phosphorylation at S473 site, reduce the Akt activation level, thereby inhibit the activity of PI3K/Akt signaling pathway, resulting in a targeted antitumor effect. Morevoer, methylacryloyl benzimidazolone derivatives have a extremely significant inhibiting effect on mTOR kinase.

Definition

As used herein, the term "substituted" refers to one or more hydrogen atoms on a group are substituted with a substituent selected from the group consisting of C1~C10 alkyl, C3~C10 cycloalkyl, C1~C10 alkoxy, halo, hydroxy, carboxy (—COOH), C1~C10 aldehyde group, C2~C10 acyl, C2~C10 ester group, amino, phenyl; the phenylincludes unsubstituted phenyl or substituted phenyl having 1 to 3 substituents, the substituent is selected from the group consisting of halogen, C1-C10 alkyl, cyano, OH, nitro, C3~C10 cycloalkyl, C1~C10 alkoxy, amino.

The term "C1~C10 alkyl" refers to a linear or branched alkyl having 1 to 10 carbon atoms, such as methyl, ethyl, propyl, isopropyl, butyl, isobutyl, sec-butyl, tert-butyl, or their similar groups.

The term "C3~C10 cycloalkyl" refers to a cycloalkyl having 3 to 10 carbon atoms, such as cyclopropyl, cyclobutyl, cyclopentyl, cycloheptyl, or their similar groups.

The term "C2~C10 alkenyl" refers to an alkenyl having 1 to 10 carbon atoms, e.g., ethenyl, propenyl, isopropenyl, butenyl, isobutenyl, sec-butenyl, tert-butenyl, or their similar groups.

The term "C2~C10 alkynyl" refers to an alkynylhaving 1 to 10 carbon atoms, e.g., ethynyl, propynyl, iso-propynyl, butynyl, isobutynyl, sec-butynyl, tert-butynyl, or their similar groups.

The term "C6~C10 aryl" refers to an aryl having 6 to 10 carbon atoms, including monocyclic or bicyclic aryl, e.g., phenyl, naphthyl, or their similar groups.

The term "C1~C10 heteroaryl" refers to a heteroaryl having 1 to 10 carbon atoms, e.g., pyrrolyl, pyridyl, furyl, or their similar groups.

The term "C1~C10 alkoxy" refers to a linear or branched alkoxy having 1 to 10 carbon atoms, such as methoxy, ethoxy, propoxy, isopropoxy, butoxy, isobutoxy, sec-butoxy, tert-butoxy, or their similar groups.

The term "C6~C10 aryloxy" refers to a linear or branched aryloxy having 6 to 10 carbon atoms, e.g., phenyloxy, naphthyloxy, or their similar groups.

The term "C1~C10 heteroaryloxy" refers to a linear or branched heteroaryloxy having 1 to 10 carbon atoms, such as pyridyloxy, furyloxy, or their similar groups.

The term "C1~C10 acyl" refers to a "—CO-alkyl" structure, preferably a "—CO—C1~C10 alkyl" structure, such as methyl acyl, ethyl acyl, propyl acyl, isopropyl acyl, butyl acyl, isobutyl acyl, sec-butyl acyl, tert-butyl acyl, or their similar groups.

The term "C1~C10 ester group" refers to an alkyl-COO— structure, preferably a C1~C10 alkyl-COO— structure, e.g., $CH_3COO$—, $C_2H_5COO$—, $C_3H_8COO$—, $(CH_3)_2CHCOO$—, $nC_4H_9COO$—, $tC_4H_9COO$—, or their similar groups. The term "C1~C10 sulfonyl" refers to an "—$SO_2$-alkyl" structure, preferably a "—$SO_2$-C1~C10 alkyl" structure, e.g., methylsulfonyl, ethylsulfonyl, propylsulfonyl, isopropylsulfonyl, butylsulfonyl, iso-butylsulfonyl, sec-butylsulfonyl, tert-butylsulfonyl, or their similar groups.

The term "C1~C20 heterocycloalkyl" refers to a heterocycloalkyl having 1 to 20 carbon atoms, such as oxiranyl, tetrahydrofuryl, tetrahydropyrrolyl, or their similar groups.

The term "halogen" refers to F, Cl, Br or I.

Active Ingredient

In present invention, "the compound of the present invention", "the compound of FD Series of the present invention" and "the active ingredient of the present invention", which can be used interchangeably, refer to methylacryloyl benzimidazolone derivatives (methylacryloyl benzimidazole (thio) ketone derivatives), or an optical isomer thereof, a pharmaceutically acceptable salt or prodrug thereof.

In the present invention, a kind of methylacryloyl benzimidazolone derivatives have the structure as shown in Formula I,

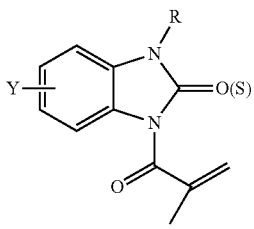

(I)

in formula I, R, Y are defined as above.

In addition, in the formula, "=O (S)" represents "=O" (ketone) or "=S" (thione).

In the present invention, in a particularly preferred kind of methylacryloyl benzimidazole (thio) ketone derivatives, R represents hydrogen, propenyl, isopropenyl, 2-fluoroethyl, 2-chloroethyl, 2-bromoethyl, 2-methoxyethyl, 2-methoxypropyl, 2-methoxy isopropyl;

Y represents:

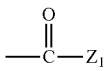

wherein, $Z_1$ represents: hydroxy, methoxy, ethoxy, n-propoxy, isopropoxy, n-butoxy.

Representative methylacryloyl benzimidazolone derivatives include those compounds (shown below) as disclosed in Tables 1-4 in CN201110326737, or a pharmaceutically acceptable salt thereof:

(1) compounds IA-01 to IA-195;
(2) compounds Ia-01 to Ia-195;
(3) compounds IB-01 to IB-195;
(4) compounds Ib-01 to Ib-195;
(5) compounds IC-01 to IC-195;
(6) compounds Ic-01 to Ic-195;
(7) compounds ID-01 to ID-195;
(8) compounds Id-01 to Id-195;
(9) compounds IIA-01 to IIA-45;
(10) compounds IIa-01 to IIa-45;
(11) compounds IIB-01 to IIB-45;
(12) compounds llb-01 to IIb-45;
(13) compounds IIC-01 to IIC-45;
(14) compounds IIc-01 to IIc-45;
(15) compounds IID-01 to IID-45;
(16) compounds IId-01 to IId-45;
(17) compounds IIIA-01 to IIIA-60;
(18) compounds IIIa-01 to IIIa-60;
(19) compounds IIIB-01 to IIIB-60;
(20) compounds IIIb-01 to IIIb-60;
(21) compounds IIIC-01 to IIIC-60;
(22) compounds IIIc-01 to IIIc-60;
(23) compounds IIID-01 to IIID-60;
(24) compounds IIId-01 to IIId-60;
(25) compounds IVA-01 to IVA-51;
(26) compounds IVa-01 to IVa-51;
(27) compounds IVB-01 to IVB-51;
(28) compounds IVb-01 to IVb-51;
(29) compounds IVC-01 to IVC-51;
(30) compounds IVc-01 to IVc-51;
(31) compounds IVD-01 to IVD-51;
(32) compounds IVd-01 to IVd-51.

Pharmaceutically Acceptable Salts or Prodrugs

The compounds of the present invention also include the pharmaceutically acceptable salts of the methylacryloyl benzimidazole (thio) ketone derivatives as shown in Formula I.

As used herein, the term "pharmaceutically acceptable salt" refers to salts formed by a compound of the present invention with a pharmaceutically acceptable inorganic and organic acid. The inorganic acid includes: hydrochloric acid, hydrobromic acid, phosphoric acid, nitric acid, sulfuric acid; and the organic acid includes: formic acid, acetic acid, propionic acid, succinic acid, naphthalene disulfonic acid (1,5), asiatic acid, oxalic acid, tartaric acid, lactic acid, salicylic acid, benzoic acid, pentanoic acid, diethyl acetic acid, malonic acid, succinic acid, fumaric acid, pimelic acid, adipic acid, maleic acid, malic acid, sulfamic acid, phenylpropionic acid, gluconic acid, ascorbic acid, nicotinic acid, isonicotinic acid, methanesulfonic acid, p-toluenesulfonic acid, citric acid, and amino acid. The term "pharmaceutically acceptable salt" may also refer to the sodium salt, potassium salt or ammonium salt of the compounds of the present invention.

As used herein, the term "pharmaceutically acceptable prodrug" refers to a compound that is inactive in vitro but capable of being converted into the active substance of Formula I in vivo, therby to exert its pharmacological action.

Pharmaceutical Composition

The present invention also provides a pharmaceutical composition, which has a significant anti-tumor effect, comprising a therapeutically effective amount of a compound of Formula I, or a pharmaceutically acceptable salt thereof, and one or more pharmaceutically acceptable carriers. In another preferred embodiment of the present invention, the pharmaceutical composition comprises a therapeutically effective amount of anagrelide hydrochloride, and one or more pharmaceutically acceptable carriers.

A mixture formed by a compound itself or a pharmaceutically acceptable salt thereof with a medicinal excipient, diluent or the like, can be orally administered in the form of tablets, capsules, granules, powders or syrups, or non-orally administered in the form of injection. The pharmaceutical composition preferably contains 0.01-99wt % of the compound of Formula I or a pharmaceutically acceptable salt thereof as an active ingredient, and more preferably contains 0.1-90wt % of the active ingredient.

The above formulations may be prepared by conventional methods of pharmacy. Examples of available medicinally adjuvants include excipients (e.g. sugar derivatives such as lactose, sucrose, glucose, mannitol and sorbitol; starch derivatives such as corn starch, potato starch, dextrin and carboxymethyl starch; cellulose derivatives such as crystalline cellulose, hydroxypropyl cellulose, carboxymethyl cellulose, calcium carboxymethyl cellulose, sodium carboxymethyl cellulose; gum arabic; dextran; silicate derivative such as metasilicate magnesium aluminum; phosphate derivatives such as calcium phosphate; carbonate derivatives such as calcium carbonate; sulfate derivatives such as calcium sulfate), binders (e.g., gelatin, polyvinyl pyrrolidone, and polyethylene glycols), disintegrants (e.g., cellulose derivatives such as sodium carboxymethyl cellulose, polyvinylpyrrolidone), lubricants (e.g., talc, calcium stearate, magnesium stearate, spermaceti, boric acid, sodium benzoate, leucine), stabilizers (methyl paraben, propyl paraben, etc.), flavoring agents (e.g., common sweeteners, sour agents, perfumes and the like), diluents and injection solvents (such as water, ethanol, glycerol, etc.).

The dose of the compounds of the present invention, pharmaceutically acceptable salts or prodrugs thereof, or pharmaceutical compositions thereof varies with age, gender, race, and conditions. The daily dose for a adult is about 10 mg-2000 mg, preferably 50 mg-1000 mg, generally.

PI3K/Akt/mTOR Signaling Pathway

The present invention finds that methylacryloyl benzimidazolone derivatives can inhibit PI3K/Akt signaling pathway. Therefore, it has many functions such as regulating cell cycle (arresting effect), inhibiting the growth of tumor cell, inducing apoptosis and so on, and can be applied in the treatment of tumors and the like.

In one embodiment of the present invention, the enzyme-linked immunosorbent assay results show methylacryloyl benzimidazolone derivatives (FD series) could significantly inhibit Akt phosphorylation at 5473 site, and reduce Akt activation levels, thereby inhibit the activity of PI3K/Akt signaling pathway, to achieve a targeted anti-tumor effect.

In one embodiment of the present invention, the protein electrophoresis results indicate that the compounds of the present invention could significantly inhibit the Akt phosphorylation at the cellular level after the compounds of the present invention act on tumor cells (such as A549 cells) for a period of time.

In one embodiment of the present invention, the results of sulforhodamine B method show that compound FD1 of the FD series compounds of the present invention could significantly inhibit the proliferation of tumor cell lines with high selectivity, and it has a more potent inhibiting effect on the growth of PTEN-deficient PC-3 cells line.

PI3K

PI3K are important intracellular signal transduction molecules, which can be divided into three classes, based on the structural characteristics of P110 subunit and different substrates of PI3K, and the function of Class I is most important.

PI3K is mainly composed of a catalytic subunit P110 and a regulatory subunit P85. PI3K can be activated by external signals, including growth factors, cytokines, hormones and so on. PI3K activation makes phosphoinositides phosphorylation in the cell membrane. It converts 3-hydroxy of inositol ring into phosphatidylinositol 3,4-bisphosphate PtdIns (PI-3,4P2) and phosphatidylinositol 3,4,5-trisphosphate (PI-3,4,5P3), and both of them can be used as a second messenger to convey signals and mediate variouscellular functions of PI3K, for example, these lipid products can activate Akt by binding to the PH (pleckstrin homology) domain of Akt. The expressing product of the tumor suppressor gene PTEN (phosphatase and tensinhomologdeletedonchromosometen) can induce dephosphorylation of 3 phosphoinositide, therebynegatively regulate PI3K pathway.

Akt

Akt is a Ser/Thr protein kinases. With the synergistic action of phosphatidylinositol-dependent protein kinase (PDK), PI-3,4P2 and PI-3,4,5P3 can bind Akt, makeing that Akt translocates from the cytoplasm to the cell membrane, and promoting the Akt phosphorylation at Ser473 and Thr308.

The phosphorylation at Ser473 and/or Thr308 is a necessary condition for Akt activationwhich is an important prerequisite for its function of promoting cell survival. Activated Akt exerts its wide biological effects, including anti-apoptosis, promoting cell survival and other functions, primarily through promoting the phosphorylation of Bad (pro-apoptotic member of Bcl-2 family), mTOR, Caspase 3, glycogen synthase kinase −3 (GSK −3) and other downstream substrates.

mTOR mTOR is also called FRAP (FKBP-rapamycin-associated protein), which belongs to a family of phosphoinositide kinase 3-related kinase (PIKKs), is a downstream substrate of PI3K/Akt, and can start the translation process by changing the phosphorylation status of translation regulatory factor 4EBP1 (eukaryotic cell initiation factor 4E binding protein) and p70S6k.

Dephosphorylated 4EBP1 can bind to translation initiation factor eIF-4E thereby inactivating eIF-4E; while phosphorylated 4EBP1 can dissociate and release eIF-4E, so as to making eIF-4E bind to mRNA 5' end of the starting point to start the translation process. Phosphorylation of p70S6k can promote phosphorylation of 40S ribosomal protein S6 to start translation . PI3K/Akt/mTOR signaling pathway plays an important role in both normal and tumor cell proliferation and survival, and the antitumour drugs working mainly by inhibiting mTOR have entered the early clinical stages.

Cell Cycle Regulation

The present invention provides a method for regulating cell cycle comprising a step of administering to a cell an effective amount of a compound of Formula I or a pharmaceutical composition comprising a compound of Formula I.

Preferably, the compounds of Formula I may be used to arrest cell cycle, such as inducing G1 cell cycle arrest, thereby regulating cell cycle, or alter cell division process.

The compounds of Formula I or a pharmaceutical composition thereof can selectively regulate cell cycle of some cells, while as for the other non-sensitive cells these compounds do not induce cell cycle arrest. In a preferred embodiment of the present invention, the compounds of Formula I, or a pharmaceutical composition thereof are used to regulate the cell cycle of tumor cell.

In another preferred embodiment, the tumor cell is selected from a group consisting of: Hela, H4, FHCC98, SMMC7721, BEL7404, A498, SW1116, MDA-MB-231, MDA-MB-468, DU145, U87- MG, Wi38, H1299 cells, or the combinations thereof; preferably selected from the group of: Hela, H4, FHCC98, SMMC7721 cells, or the combinations thereof.

The compounds of Formula I can act on cells and induce or regulate cell cycle to generate cell cycle arrest at a lower concentration, preferably at a concentration of ≤1 mM/L. In another preferred embodiment, the effective concentration of the compound of Formula I is 0.01 nM/L-1 mM/L, preferably 0.1 nM/L-500 μM/L, and most preferably 1 nM/L-100 μM/L.

The action time of the compounds of Formula I, not particularly limited, may be, for example, 2h~30 days. Preferably the action time of the compounds of Formula I will vary depending on the acting environmentand the subject. In a preferred embodiment of the present invention, the action time of the compounds of Formula I is 2 to 96h. In another preferred embodiment, the action time of the compounds of Formula I is 1 to 30 days.

Apoptosis Induction

The present invention provides a method for inducing apoptosis or inhibiting cell growth comprising a step of administering to a cell an effective amount of a compound of Formula I or a pharmaceutical composition comprising a compound of Formula I.

The compounds of Formula I or a pharmaceutical composition thereof can selectively induce apoptosis or inhibite cell growth for some cells, while not inhibite the growth of other non-sensitive cells.

In a preferred embodiment of the present invention, the compounds of Formula I or a pharmaceutical composition thereof is used to regulate the cell cycle of a tumor cell. Preferably, the tumor cell is selected from a group consisting of: Hela, H4, FHCC98, SMMC7721, BEL7404, A498, SW1116, MDA-MB-231, MDA-MB-468, DU145, U87-MG, Wi38, H1299, or the combination thereof; preferably selected from the group of: Hela, H4, FHCC98, SMMC7721, or the combination thereof.

The compounds of Formula I can act on cells and induce or regulate cell cycle to generate cell cycle arrest at a lower concentration, preferably at a concentration of ≤100 mM/L.

In another preferred embodiment, the effective concentration of the compounds of Formula I is 0.01 nM/L-1 mM/L, preferably 0.1 nM/L-500 μM/L, and most preferably 1 nM/L-100 μM/L.

The action time of the compounds of Formula I,not particularly limited, may be, for example, 2h~30 days. Preferably the action time of the compounds of Formula I will vary depending on the acting environmentand the subject. In a preferred embodiment of the present invention, the action time of the compounds of Formula I is 2 to 96h. In another preferred embodiment, the action time of the compounds of Formula I is 1 to 30 days.

Anti-tumour Drugs

The present invention provides a method for inducing apoptosis or inhibiting cell growth, comprising a step of administering to a cell an effective amount of a compound of Formula I or a pharmaceutical composition comprising a compound of Formula I.

In a preferred embodiment of the present invention, the pharmaceutical composition comprises: (a) a therapeutically effective amount of a compound of Formula I; and (b) a pharmaceutically acceptable carrier.

In another preferred embodiment, the tumor comprises cervical cancer, glioma, and liver cancer.

In another preferred embodiment, the effective concentration of the compound of Formula I is 0.01 nM/L-1 mM/L, preferably 0.1 nM/L-500 μM/L, most preferably 1 nM/L-100 μM/L.

The present invention also provides a method for preparing an anti-tumour drug or a pharmaceutical composition, comprising a step of mixing a therapeutically effective amount of a compound of Formula I with a pharmaceutically acceptable carrier to form a pharmaceutical composition.

In another preferred embodiment, the pharmaceutical composition further comprises a component selected from the group of: tumor suppressor, tumor apoptosis inducer, or a combination thereof.

It can treat or inhibit tumors by administering a therapeutically effective amount of a compound of Formula I or a pharmaceutical composition comprising a compound of formula Ito the being treated subject.

The main advantages of the present invention are:

(1) For the first time, it has been revealed that the methylacryloyl benzimidazolone derivatives (FD series) can significantly inhibit tumor cell growth.

(2) For the first time, it has been disclosed that the methylacryloyl benzimidazolone derivatives can down-regulate the activity of PI3K/Akt pathway.

(3) For the first time, it has been revealed that the methylacryloyl benzimidazolone derivatives can reduce Akt activation levels of tumor cells.

(4) For the first time, it has been revealed that the methylacryloyl benzimidazolone derivatives can significantly inhibit the Akt phosphorylation at S473.

(5) For the first time, it has been discovered that methylacryloyl benzimidazolone derivatives can significantly inhibit the activity of mTOR kinase.

The present invention will be further illustrated below with reference to the specific examples. It should be understood that these examples are only to illustrate the invention, not to limit the scope of the invention. The experimental methods with no specific conditions described in the following examples are generally performed under the conventional conditions (e.g., the conditions described by Sambrook et al., Molecular Cloning: A Laboratory Manual (New York: Cold Spring Harbor Laboratory Press, 1989)), or according to the manufacture's instructions. Unless indicated otherwise, parts and percentage are calculated by weight.

All of the reagents and other materials used in Examples herein are commercially available, wherein unless otherwise specified, the biological reagents and materials are purchased from Shanghai Yanjing Biological Technology Co., Ltd.

EXAMPLE 1

Inhibition of Methylacryloyl Benzimidazolone Derivatives on Akt Phosphorylation

Enzyme-linked immunosorbent assay (ELISA).

Establishment of ELISA screening method using a double antibody sandwich method: A549 cells (a lung cancer cell line, purchased from Chinese Academy of Sciences, Shanghai Institutes for Biological Sciences Cell Resource Center) were inoculated at certain densities in 12-well plates, and incubated at 37° C. in a carbon dioxide incubator overnight to let cells attach the plate wells. Meanwhile the Akt antibody was inoculated at a specific concentration in a highly-adsorbed microplate, and placed in a refrigerator at 4° C. The 12-well plates were washed with sterile PBS three times, then into which serum-free F12 was added, and incubated for 24 hours in a incubator. Then MK2206, Triciribine and FD series drugs were added into 12-well plates and worked for one hour, followed by adding 100 ng of IGF-1 and being stimulated for 10 minutes. The 12-well plates were washed with pre-cooled PBS three times, and 100 μl of RIPA lysis buffer was added into each well to lyse cells on ice for 20 minutes. The lysates were collected and added to the appropriate microplate (purchased from Santa Cruz biotechnology), which were shaken on ice. A p-Akt (S473) antibody (purchased Cell Signaling Technology, Inc.) was added into microplates. After shaking for a period of time, an anti-rabbit antibody (purchased from Cell Signaling Technology, Inc.) was added. The reaction was terminated with 2M sulfuric acid after TMB developed. Absorbance at 450 nm was measured on a microplate reader, and the inhibitory rate=$(OD_{sample}-OD_{-IGF})/(OD_{IGF}-OD_{-IGF})$, among which $OD_{sample}$ refers to the absorbance of the sample well, $OD_{IGF}$ refers the absorbance of the well with IGF only, $OD_{-IGF}$ refers the absorbance of the well withoutIGF. The results were shown in Table 1. Positive controls were MK2206 and Triciribine, whose inhibitory rate to Akt phosphorylation at cell level was 92% and 46%, respectively. Amoung the compounds of the present invention, FD1 and FD3 showed an inhibitory rate to Akt phosphorylation as 85% and 91%, respectively, which were better than the positive control Triciribine and comparable with the positive control MK2206, and FD2, FD4, FD12 and FD13 showed comparable effects with that of Triciribine.

The experimental results showed that the FD series compounds (methylacryloyl benzimidazolone derivatives) have significant inhibiting effect on the Akt phosphorylation, among which the inhibiting effect of some of the compounds is comparable to that of the positive compound which has been in the clinical trial.

TABLE 1

| Compound | Structure | Inhibitory rate % |
|---|---|---|
| MK2206 | 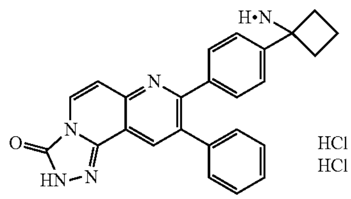 | 92% |
| Triciribine | 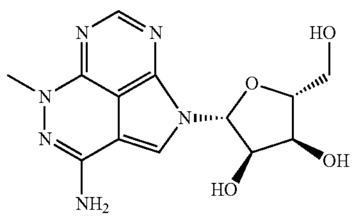 [SMILES: CN1N=C(N)c2cn([C@@H]3O[C@H](CO)[C@@H](O)[C@H]3O)c3ncnc1c23] | 46% |
| FD1 | 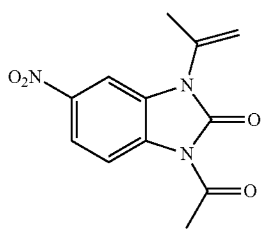 [SMILES: C=C(C)n1c(=O)n(C(C)=O)c2ccc([N+](=O)[O-])cc21] | 85% |
| FD2 | 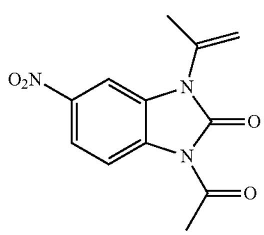 [SMILES: C=C(C)n1c(=O)n(C(C)=O)c2ccc([N+](=O)[O-])cc21] | 51% |
| FD162 | 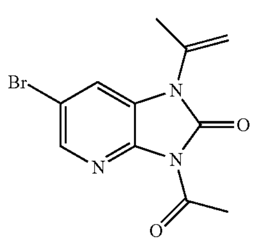 [SMILES: C=C(C)n1c(=O)n(C(C)=O)c2ncc(Br)cc21] | 91% |
| FD4 | 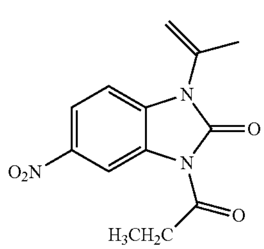 | 50% |
| FD5 | | 20% |
| FD6 | | 10% |
| FD7 | | 6% |
| FD8 | | 3% |
| FD9 | | 22% |
| FD10 | | 17% |

TABLE 1-continued

| Compound | Structure | Inhibitory rate % |
|---|---|---|
| FD11 | (5-nitro-benzimidazol-2-one, N-isopropenyl, N'-butanoyl) | 11% |
| FD12 | (6-nitro-benzimidazol-2-one, N-isopropenyl, N'-butanoyl) | 48% |
| FD13 | (5-nitro-benzimidazol-2-one, N-isopropenyl, N'-hexanoyl, -(CH₂)₄CH₃) | 56% |
| FD14 | (6-nitro-benzimidazol-2-one, N-isopropenyl, N'-hexanoyl, H₃C(H₂C)₄) | 34% |
| FD15 | (5-nitro-benzimidazol-2-one, N-isopropenyl, N'-octanoyl, -(CH₂)₆CH₃) | 42% |
| FD16 | (6-nitro-benzimidazol-2-one, N-isopropenyl, N'-octanoyl, H₃C(H₂C)₆) | 64% |
| FD17 | (5-nitro-benzimidazol-2-one, N-isopropenyl, N'-(2-methylbenzoyl)) | 38% |
| FD18 | (6-nitro-benzimidazol-2-one, N-isopropenyl, N'-(2-methylbenzoyl)) | 42% |

Western Blot

Figure 1:
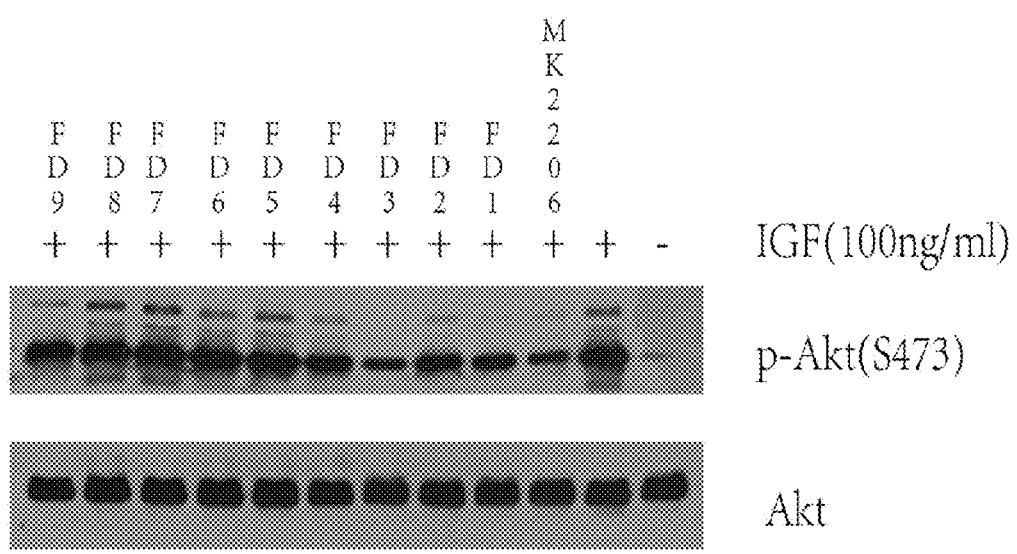
FIG. 1 shows the effect of some FD series compounds on Akt phosphorylation measured by Western blotting.

A549 cells were seeded at a density of $2\times10^5$ cells/well into 12-well plates, and adhered overnight. Then the medium was discarded and the plates were washed three times with normal saline. After that, fresh serum-free medium was added to starve cells for 24 hours, compounds to be tested were added to work for 1 h, then IGF-I was added to stimulated for 10 min, followed byadding a lysis buffer on ice to lyse for half an hour. The cell lysates were collected and centrifuged at 20000×g at 4° C. for 10min, then the supernatant was collected. Protein was quantified by MicroBCA protein quantification Assay kit, and the protein concentration was normalized. The supernatant was mixed with the 4×SDS sample buffer [200 mM Tris.Cl (pH 6.8), 400 mM DTT, 8% SDS, 0.4% bromophenol blue, 40% glycerol] and boiled for 15 min. After cooling at room temperature, aliquots were loaded on polyacrylamide gel, and electrophoresed in Tris-glycine electrophoretic buffer (25 mM Tris, 250 mM glycine, 0.1% SDS) at 80-120 V for about 2 h. Proteins were transferred from the gel to a nitrocellulose membrane by a semi-dry method. Transferring conditions: transfer buffer (39 mM glycine, 48 mM Tris base, 0.037% SDS, 20% methanol); transfer current 25 mA; transfer time 2 h. After transfer, Ponceau S staining was used to determine the transfer efficiency and the positions of protein bands on the nitrocellulose membranes. After labeling the membrane was blocked with a blocking solution containing 5% nonfat-dried milk [5% nonfat-dried milk, 20 mM Tris-HCl (pH 7.2-7.4), 150 mM NaCl, 0.1% (v/v) Tween 20] on a shaker at room temperature for 2 h. To the system were added specific primary antibodies and incubated overnight at 4° C. Then the membrane was washed with PBST solution [20 mM Tris-HCl (pH 7.2-7.4), 150 mM NaCl, 0.1% (v/v) Tween 20] at room temperature three times, 15 min/time. To the system were added Horseradish peroxidase-labeled secondary antibodies and incubated at room temperature on a shaker with gentle shaking for 2 h. After washing with PBST solution three times, the system was exposed, developed and fixed after SuperSignal West Dura Chemiluminescent Substrate (Pierce Inc, Rochford, IL) was used for color. The results were shown in FIG. 1, in which there were 12 lanes the band shade and size of which indicated the corresponding protein concentration levels. Bands in 12 lanes of Akt had comparable shade and size, indicating that each lane had a same level of total Akt; whereas bandsin the 12 lanes of p-Akt (S473)had significantly different shade and size, indicating that each lane had significantly different level of p-Akt (S473). In the signaling pathway IGF could promote a rapid increase in Akt phosphorylation levels, and in control 1 in a cell culture medium with 100 ng/ml of IGF only Akt phosphorylation level was significantly increased, while in control 2 in cell culture medium with no IGF Akt phosphorylation level was lower. MK2206 was an Akt phosphorylation inhibitor developed by Merck, and was currently in phase II clinical trial, showing good therapeutic effects in a variety of tumors. As shown in FIG. 1, the band size corresponding to MK2206 is significantly smaller than that to lontrol 1, indicating that MK2206 significantly inhibited the increase of Akt phosphorylation level stimulated by IGF. FD1 and FD3 showed comparable effects to MK2206. These experimental results showed that FD series compounds (methylacryloyl benzimidazolone derivatives) had significant inhibiting effects on Akt phosphorylation at S473 site.

EXAMPLE 2

Inhibition of Methylacryloyl Benzimidazolone Derivatives on Tumor Cells

Sulforhodamine B Method

At a certain density cells were seeded in 96-well plates, and adhered overnight. The medium was discarded after incubating cells with compounds to be tested for 72 h, then 100μL/well trichloroacetic acid (TCA) was added to fix cells at 4° C. for 2h. After that the fixing solution was discarded. Cells were gently washed 5 times with distilled water, dried at room temperature. Cells were stained with 4 mg/mL SRB staining solution (100 μL/well) at room temperature for 15min. The staining solution was discarded, and cells were washed five times with 1% acetic acid (HAC) and dried at room temperature. To the plate tris base buffer (10 mM) was added at 150 μL/well and placed at room temperature for 15min. The OD values were measured at 540 nm wavelength in a microplate reader. Inhibitory rate (%)=(OD value$_{control\ wells}$−OD value$_{drugs\ treated\ wells}$)/OD value$_{control\ wells}$×100%.

The results were shown in Table 2, the working concentrations of MK2206 and compounds of FD series were 10 μM. As shown in this Table, PC-3 is a prostate cancer cell line purchased from Cell Resource Center of Shanghai Institutes for Biological Sciences, Chinese Academy of Sciences, A549 is a lung cancer cell line purchased from Cell Resource Center of Shanghai Institutes for Biological Sciences, Chinese Academy of Sciences, and SGC-7901 is a gastric cancer cell line purchased from Cell Resource Center of Shanghai Institutes for Biological Sciences, Chinese Academy of Sciences. The results showed that FD1 could inhibit tumor cell line proliferation, and the inhibiting effects on PC-3 tumor cells (PTEN deficient) proliferation is more significant, which suggested that FD series compounds represented by FD1 had a better therapeutic effect on PTEN deficient tumortypes.

TABLE 2

| Compound | Inhibitory rate % (A549) | Inhibitory rate % (PC-3) | Inhibitory rate % (SGC-7901) |
| --- | --- | --- | --- |
| MK2206 | 61.0% | 1.2% | 24.3% |
| FD1 | 9.6% | 51.1% | 56.4% |
| FD2 | 3.4% | 32.4% | 23.4% |
| FD162 | 12.1% | 62.4% | 70.2% |
| FD4 | 7.2% | 33.9% | 22.0% |
| FD5 | 22.3% | 29.1% | 7.3% |
| FD6 | 18.2% | 24.2% | 30.4% |
| FD7 | 34.1% | 22.6% | 34.1% |
| FD8 | 2.8% | 13.4% | 28.0% |
| FD9 | 1.1% | 26.1% | 26.4% |
| FD10 | 5.3% | 13.8% | 28.1% |
| FD11 | 2.4% | 19.2% | 13.6% |
| FD12 | 3.8% | 8.2% | 19.8% |
| FD14 | 13.1% | 9.0% | 25.5% |
| FD15 | 33.3% | 4.6% | 20.1% |
| FD16 | 23.2% | 7.1% | 12.4% |
| FD17 | 31.4% | 20.0% | 40.5% |
| FD18 | 11.5% | 32.1% | 44.2% |

EXAMPLE 3

In this example, the inhibition of the following compounds to the Akt phosphorylationwas determined using the same method as described in Example 1.

The following compounds were disclosed in Tables 1 to 4 in CN201110326737:
  (1) IA-01 and IA-162 in compounds IA-01 to IA-195;
  (2) Ia-05 and Ia-134 in compounds Ia-01 to Ia-195;
  (3) IB-07 and IB-075 in compounds IB-01 to IB-195;
  (4) Ib-07 and Ib-09 in compounds Ib-01 to Ib-195;
  (5) IC-137 in compounds IC-01 to IC-195;
  (6) Ic-06 and Ic-135 in compounds Ic-01 to Ic-195;
  (7) ID-014 in compounds ID-01 to ID-195;
  (8) Id-01 in compounds Id-01 to Id-195;
  (9) IIA-41 in compounds IIA-01 to IIA-45;
  (10) IIa-13 and IIa-39 in compounds IIa-01 to IIa-45;
  (11) IIB-08 and IIB-32 in compounds IIB-01 to IIB-45;
  (12) IIb-46 in compounds IIb-01 to IIb-45;
  (13) IIC-26 in compounds IIC-01 to IIC-45;
  (14) IIc-16 in compounds IIc-01 to IIc-45;
  (15) IID-32 in compounds IID-01 to IID-45;
  (16) IId-17 and IId-36 in compounds IId-01 to IId-45;
  (17) IIIA-03 and IIIA-37 in compounds IIIA-01 to IIIA-60;
  (18) IIIa-01 in compounds IIIa-01 to IIIa-60;
  (19) IIIB-60 in compounds IIIB-01 to IIIB-60;
  (20) IIIb-60 in compounds IIIb-01 to IIIb-60;
  (21) IIIC-14 in compounds IIIC-01 to IIIC-60;
  (22) IIIc-27 and IIIc-59 in compounds IIIc-01 to IIIc-60;
  (23) IIID-29 in compounds IIID-01 to IIID-60;
  (24) IIId-27 in compounds IIId-01 to IIId-60;
  (25) IVA-51 in compounds IVA-01 to IVA-51;
  (26) IVa-43 in compounds IVa-01 to IVa-51;
  (27) IVB-38 and IVB-45 in compounds IVB-01 to IVB-51;
  (28) IVb-28 in compounds IVb-01 to IVb-51;
  (29) IVC-05 and IVC-27 in compounds IVC-01 to IVC-51;
  (30) IVc-37 in compounds IVc-01 to IVc-51;
  (31) IVD-13 and IVD-46 in compounds IVD-01 to IVD-51;
  (32) IVd-47 in compounds IVd-01 to IVd-51.

The results showed that all the tested compounds had significant inhibiting effects to the Akt phosphorylation. When the concentration of the compound was 10μM, the inhibitory rate of Aid phosphorylation was 3% -91%, most (more than ¾) of which the inhibitory rate was 30% -60%.

EXAMPLE 4

Inhibition Test to Tumor-associated Kinase

In the present invention we investigated the inhibiting activity of the compound FD162 to 114 tumor-associated kinases, and found that FD162 (at the concentration of 10 μM) could selectively inhibit the activity of mTOR. Eurofins Pharma Discovery Services UK Limited completed and reported this experiment. The results were shown as below.

| Kinase name | Inhibitory rate (%) | Kinase name | Inhibitory rate (%) | Kinase name | Inhibitory rate (%) |
|---|---|---|---|---|---|
| Abl(h) | 2 | FGFR3(h) | 7 | PKCγ(h) | 11 |
| Abl(T315I)(h) | −14 | Flt3(h) | 4 | PKCδ(h) | 18 |
| ALK(h) | 16 | Fms(h) | −9 | PKCε(h) | −1 |
| Arg(h) | −7 | Fyn(h) | 2 | PKCη(h) | 2 |
| ASK1(h) | 4 | GSK3β(h) | 6 | PKCι(h) | 11 |
| Aurora-A(h) | 1 | IGF-1R(h), activated | 0 | PKCμ(h) | 6 |
| Axl(h) | 24 | IKKα(h) | 5 | PKCθ(h) | −3 |
| Blk(h) | −5 | IRAK1(h) | 9 | PKCζ(h) | 5 |
| Bmx(h) | −7 | Itk(h) | −7 | PKD2(h) | 11 |
| BTK(h) | 7 | JAK2(h) | 7 | Plk1(h) | 7 |
| B-Raf(h) | −6 | JNK1α1(h) | 4 | PRAK(h) | 10 |
| B-Raf(V599E)(h) | −1 | JNK2α2(h) | 3 | PRK2(h) | −9 |
| CaMKI(h) | −1 | KDR(h) | −1 | Ret(h) | 7 |
| CaMKIIβ(h) | 2 | Lck(h)activated | −1 | ROCK-I(h) | −4 |
| CaMKIV(h) | 2 | LKB1(h) | 8 | Ron(h) | 8 |
| CaMKK2(h) | 1 | MAPK1(h) | 8 | Ros(h) | −13 |
| CDK1/cyclinB(h) | 1 | MAPK2(h) | −6 | Rsk1(h) | 9 |
| CDK2/cyclinA(h) | −2 | MEK1(h) | −2 | Rsk2(h) | 4 |
| CDK2/cyclinE(h) | 0 | MARK1(h) | −1 | Rsk3(h) | 2 |
| CDK3/cyclinE(h) | 7 | Met(h) | −9 | SGK(h) | −4 |
| CDK5/p35(h) | 0 | MKK6(h) | 5 | Syk(h) | 0 |
| CDK6/cyclinD3(h) | −1 | MST2(h) | 1 | Tie2(h) | 14 |
| CDK7/cyclinH/MAT1(h) | −8 | mTOR/FKBP12(h) | 33 | Yes(h) | −2 |
| CHK1(h) | −14 | NEK2(h) | −6 | ZAP-70(h) | −5 |
| CHK2(h) | 4 | p70S6K(h) | 3 | PI3Kinase(p110β/p85α)(h) | −3 |
| CK1δ(h) | 7 | PAK2(h) | 8 | PI3Kinase(p120γ)(h) | 2 |
| CK2(h) | 15 | PAR-1Bα(h) | 6 | PI3Kinase(p110δ/p85α)(h) | 3 |
| cKit(h) | 7 | PEK(h) | 0 | PI3Kinase(p110α/p85α)(h) | −1 |
| CSK(h) | −12 | PDGFRα(h) | −9 | PI3Kinase(p110α(E542K)/p85α)(h) | 4 |
| c-RAF(h) | −3 | PDGFRβ(h) | −8 | PI3Kinase(p110α(H1047R)/p85α)(h) | 3 |
| cSRC(h) | −4 | PDK1(h) | −1 | PI3Kinase(p110α(E545K)/p85α)(h) | 4 |
| DYRK2(h) | 1 | Pim-1(h) | 3 | PI3Kinase(p110α/p65α)(h) | 3 |
| EGFR(h) | 0 | PKA(h) | −5 | PI3KC2α(h) | 7 |
| EphB2(h) | 7 | PKBα(h) | 4 | PI3KC2γ(h) | 3 |
| EphB4(h) | −8 | PKBβ(h) | 4 | PIP4K2α(h) | −2 |
| FAK(h) | 1 | PKBγ(h) | 8 | PIP5K1α(h) | −2 |
| Fes(h) | −8 | PKCα(h) | 24 | PIP5K1γ(h) | −1 |
| FGFR1(h) | 4 | PKCβII(h) | 6 | mTOR(h) | 95 |

EXAMPLE 5

Inhibition of Compounds to the Proliferation of Tumor Cell Lines

In the present invention the inhibition of a representative compound FD162 to the proliferation of more than 20 tumor cell lines were tested, and the experimental methods were the same as that described in Example 2. The results shown in FIG. 2 showed widespread inhibitory effects of FD162 to the proliferation of tumor cells, among which the half inhibitory concentration of FD162 to Hela cell proliferation was 3.67 micromole.

EXAMPLE 6

Inhibition Test to Signaling Pathway

Using the method of Example 1, the effect of different concentrations of FD162 on signal pathways was tested at the cellular level. As shown in FIG. 4, FD162 could down-regulate PI3K/Akt/mTOR signaling pathway in a dose-dependent manner. RAD is everolimus which was an anti-tumour drug as an mTOR inhibitor, its concentration is 10 μM; Rapa was rapamycin; MK was MK2206 which was an anticancer drug in clinical trial as an Akt inhibitor.

EXAMPLE 7

Animal Experiment

The method used herein for animal experiment was that using the subcutaneous transplantation of Hela cells into nude mice.

Detailed Experiemental Methods Were as Follows:

Tumor tissues at vigorous growth phase were cut into the size of about 1.5mm³, and inoculated subcutaneously to the right armpit of nude mice under sterile condition. The diameters of subcutaneous xenograft tumors in nude mice were measured with a vernier caliper. The animals were randomly divided when the tumors grew to the sizes of 100-200 mm³. FD162 was divided into three groups: 20mg/kg, 10mg/kg and 5mg/kg, with 9 mice per group; rapamycin was 10mg/kg; the model group was given saline. All treatments were intraperitoneally administered once a day for 12 days. Throughout the experiment, tumor diameters and body weights were measured simultaneously twice a week. Tumor volume (TV) was calculated as follows: TV=½×a×b2, where a, b respectively represents the length and width of tumors. The relative tumor volume (RTV) was calculated based on the results of the measurements as follows: RTV=Vt/V0, in which, V0 was the measured tumor volume at the start of group division (i.e. d0), and Vt was the measured tumor volume each time.The evaluation index of anti-tumor activity are 1) relative tumor proliferation rate T/C (%), calculated as follows: T/C (%)=(TRTV/CRTV)×100%, TRTV: RTV of treatment group; CRTV: RTV of negative control group; 2) tumor volume growth inhibitory rate GI %, calculated as follows: GI %=[1-(TVt-TV0)/(CVt-CT0)]×100%, TVt is the tumor volume of treatment groups at each measurement; TV0 is the tumor volume of treatment groups at the start of group division; CVt is the tumor volume of control groups at each measurement; CV0 is the tumor volume of control groups at the start of group division; 3) tumor weight inhibitory rate, calculated as follows: tumor weight inhibitory rate %=(Wc−WT)/Wc×100%, Wc: tumor weight of control group, WT: tumor weight of treatment group.

Experimental results showed that the compound FD162 of the present invention achieved the best tumor inhibiting effect at the middle dose (10 mg/kg), better than the positive control group. A tumor inhibitory rate of greater than 50% was achieved after administration of this drug at the middle dose (10 mg/kg) for 12 days. Tumor inhibiting effects were shown in FIG. 5.

EXAMPLE 8

Preparation of Compound FD162

Compound FD162discolsed in the present invention can be prepared using the following synthesis scheme.

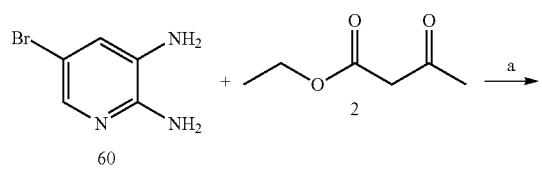

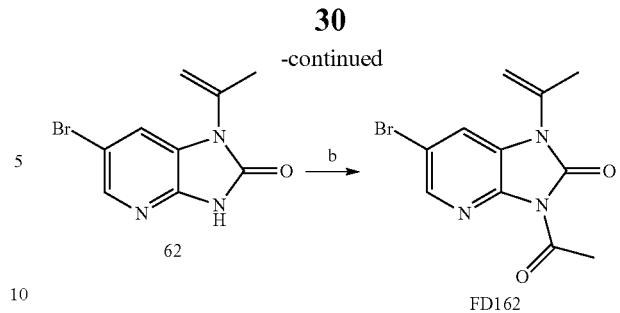

Detailed experimental steps are as follows:

Synthesis of Intermediate 62. 187.0 g (1 mol) of 5-bromo-2,3-diaminopyridine (60), 450 mL of xylene, and 5 mL of an ethanol solution of potassium hydroxide (in which the weight of potassium hydroxide was 1.0 g) were added into a three necked-reaction flask equipped with a Dean-Stark trap. After heating and stirring at reflux, a mixture of 156.0 g (1.2 mol) of ethyl acetoacetate (2) and 160 mL of xylene was slowly added dropwise. Then the mixture was stirred at reflux and azeotropic dehydrated until no water drops appeared, and stirred at reflux for another 2h. After the reaction completed, the mixture was cooled. The precipitated crystals were filtered and dried to yield 235.5 g (yield 93.1%) of a white granular crystal, i.e. 6-bromo-1-isopropenyl -1H-imidazo [4,5] pyridin-2(3H)-one (62) with a melting point (m.p.) of 130~132° C. Mass spectrum (ESI, positive ion mode) [m+H] m/z 254.

Synthesis of FD162. 2.53g (0.01mol) of 6- bromo-1-isopropenyl -1H- imidazo [4,5] pyridin −2(3H)-one (62) and 50 mL of dehydrated dichloromethane were added into a three necked-reaction flask, and the mixture was stirred until complete dissolution, then 2 mL of triethylamine was added. 0.86 g (0.011 mol) of acetyl chloride was added dropwise in ice-bath. After addition, the mixture was stirred at room temperature for 5~8h. After completion of the reaction, 50 mL of saturated sodium bicarbonate solution was added. The mixture was stirred for another 15 min, then transferred into a separatory funnel. The aqueous phase was discarded, and the organic phase was washed with water and saturated sodium chloride solution, and dried with anhydrous sodium sulfate, and then the solvent was removed under reduced pressure. The concentrate was purified by column chromatography on silica gel (the eluent was petroleum ether/ethyl acetate=6/1) to obtain 2.72 g of FD162 (yield 92.2%) with a melting point (m.p.) of 136~138° C. Mass spectrum (ESI, positive ion mode) [M+H]⁺ m/z 296. ¹ H NMR (CDCl₃), δ 2.23(s, 3H), 2.76(s, 3H), 5.35(s, 1H), 5.51(s, 1H), 8.23(d, J=2.0Hz, 1H), 8.53(d, J=2.0Hz, 1H); ¹³C NMR (CDCl₃), δ 20.2, 25.6, 114.1, 116.2, 121.5, 125.2, 135.2, 141.9, 144.4, 149.9, 170.2.

Discussion

The methylacryloyl benzimidazolone derivatives of the present invention can down-regulate the Akt phosphorylation level in the Pl3K/Akt signaling pathway, and the effect is comparable to that of the novel small molecule targeted drug MK2206. The study at the cellular level indicates that the methylacryloyl benzimidazolone derivatives represented by FD1 have a good proliferation inhibiting effect on tumor cells, and what is different from MK2206 is that FD1 has better effects on PTEN-deficient cells.

The methylacryloyl benzimidazolone derivatives of the present invention have a remarkable inhibiting effect on mTOR kinase and can be developed as a mTOR kinase inhibitor for tumor therapy.

All documents referred in the present invention are incorporated by reference as if each reference is cited alone as a reference in the present application. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A compound or a pharmaceutically acceptable salt thereof, wherein the compound has the following structural formula:

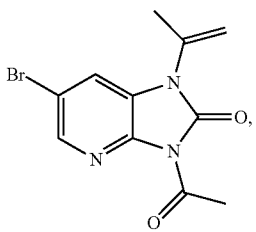 [SMILES: C=C(C)n1c(=O)n(C(C)=O)c2ncc(Br)cc21]

2. A pharmaceutical composition, comprising the compound of claim 1 or a pharmaceutically acceptable salt thereof; and a pharmaceutically acceptable carrier.

3. The pharmaceutical composition of claim 2, further comprising a methylacryloylbenzimidazolone derivative of Formula I, or an optical isomer thereof, or a pharmaceutically acceptable saltthereof, or a prodrug thereof, wherein the Formula I is

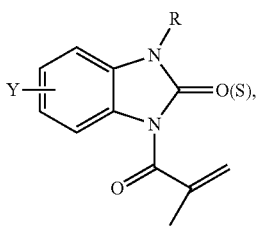

where R represents: hydrogen; $C_1$~$C_8$ alkyl or $C_1$~$C_8$ alkyl optionally substituted by cyano, halogen, benzene ring, $C_1$~$C_4$ alkoxy or $C_1$~$C_4$ alkylthio; $C_3$~$C_8$ alkenyl or $C_3$~$C_8$ alkynyl; or $C_3$~$C_8$ alkenyl or $C_3$~$C_8$ alkynyl optionally substituted by cyano, halogen, $C_1$~$C_4$ alkoxy or $C_1$~$C_4$ alkylthio; phenyl or phenyl optionally substituted by 1~3 substituents selected from the group consisting of halogen, $C_1$~$C_8$ alkyl, $C_3$~$C_8$ cycloalkyl, hydroxyl, $C_1$~$C_4$ alkoxy, $C_1$~$C_4$ haloalkyl, $C_1$~$C_4$ haloalkoxy, $C_1$~$C_4$ haloalkylthio, $C_1$~$C_4$ haloalkyl sulfonyl, carboxy, nitro, cyano, phenyl, phenoxy, and benzoyl, Y represents hydrogen or 1~4 substituents selected from the group consisting of: halogen, nitro, $C_1$~$C_8$ alkyl, $C_3$~$C_8$ cycloalkyl, and $C_1$~$C_4$ haloalkyl, wherein R is not isopropenyl when Y represents hydrogen, or Y represents

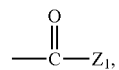

where $Z_1$ represents hydroxyl, $C_1$~$C_8$ alkoxy, $C_3$~$C_8$ alkenyloxy or $C_3$~$C_8$ alkynyloxy, amino, or amino substituted with one or two $C_1$~$C_8$ alkyl, or Y represents —O(S)—$Z_2$, where $Z_2$ represents hydrogen, $C_1$~$C_4$ alkyl, $C_3$~$C_8$ alkenyl or $C_3$~$C_8$ alkynyl, $C_1$~$C_4$ haloalkyl, $C_1$~$C_8$ aliphatic acyl, $C_1$~$C_8$ haloaliphatic acyl, carbamoyl, N-methylcarbamoyl, N-ethylcarbamoyl, N, N-dimethylcarbamoyl, N, N-diethylcarbamoyl, phenyl, benzoyl, phenylacetyl, phenylsulfonyl; or phenyl, benzoyl or phenylsulfonyl optionally substituted with 1~3 substituents selected from the group consisting of: halogen, $C_1$~$C_8$ alkyl, $C_3$~$C_8$ cycloalkyl, hydroxyl, $C_1$~$C_4$ alkoxy, $C_1$~$C_4$ haloalkyl, $C_1$~$C_4$ haloalkoxy, $C_1$~$C_4$ haloalkylthio, $C_1$~$C_4$ haloalkylsulfonyl, carboxy, nitro, and cyano, or Y represents

where $Z_3$ represents hydrogen, $C_1$~$C_8$ alkyl, $C_3$~$C_8$ cycloalkyl, $C_3$~$C_8$ alkenyl, $C_3$~$C_8$ alkynyl, $C_1$~$C_4$ haloalkyl, $C_1$~$C_8$ acyl; or a 5- or 6-membered heterocyclic group having 1 to 3 heteroatoms selected from nitrogen, oxygen and sulfur; phenyl, benzoyl, phenylacetyl, phenylsulfonyl; or phenyl, benzoyl or phenylsulfonyl optionally substituted with 1~3 substituents selected from the group consisting of: halogen, $C_1$~$C_8$ alkyl, $C_3$~$C_8$ cycloalkyl, hydroxy, $C_1$~$C_4$ alkoxy, $C_1$~$C_4$ haloalkyl, $C_1$~$C_4$ haloalkoxy, $C_1$~$C_4$ haloalkylthio, $C_1$~$C_4$ haloalkylsulfonyl, carboxy, nitro, cyano; $Z_4$ represents hydrogen, $C_1$~$C_8$ alkyl, $C_3$~$C_8$ cycloalkyl, $C_3$~$C_8$ alkenyl, $C_3$~$C_8$ alkynyl, $C_1$~$C_4$ haloalkyl, or $Z_3$ and $Z_4$ is connected by a nitrogen atom to form a 5~7-membered heterocyclic group which may contain one or two or more than two heteroatoms selected from nitrogen and oxygen.

4. A non-therapeutic method in vitro for down-regulating the activity of PI3K/Akt pathway and/or regulating cell cycle, comprising:
culturing cell in the presence of the compound of claim 1.

5. A non-therapeutic method in vitro for inhibiting cell growth or inducing apoptosis comprising:
culturing cell in the presence of the compound of claim 1.

6. A kit, comprising: a container; and the compound of claim 1 or a pharmaceutically acceptable salt thereof.

7. The kit of claim 6, further comprising a specification describing use of the compound of claim 1 or a pharmaceutically acceptable salt thereof for one or more applications selected from the group consisting of:
(i) inhibiting tumor cell growth;
(ii) inducing tumor cell apoptosis;
(iii) down-regulating the activity of PI3K/Akt pathway;
(iv) reducing mTOR activation level.

* * * * *